United States Patent
Stadtmueller et al.

(10) Patent No.: US 7,371,753 B2
(45) Date of Patent: *May 13, 2008

(54) DIHYDROPTERIDINONES, PROCESSES FOR PREPARING THEM AND THEIR USE AS PHARMACEUTICAL COMPOSITIONS

(75) Inventors: Heinz Stadtmueller, Gaweinstal (AT); Harald Engelhardt, Ebreichsdorf (AT); Andreas Schoop, Vienna (AT); Martin Steegmaier, Vienna (AT); Matthias Hoffmann, Mittelbiberach (DE); Matthias Grauert, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 15 days.

This patent is subject to a terminal disclaimer.

(21) Appl. No.: 11/211,783

(22) Filed: Aug. 25, 2005

(65) Prior Publication Data

US 2006/0046990 A1  Mar. 2, 2006

(30) Foreign Application Priority Data

Aug. 27, 2004 (EP) .................................. 04020339

(51) Int. Cl.
| | |
|---|---|
| A61K 31/5025 | (2006.01) |
| A61K 31/496 | (2006.01) |
| A61K 31/551 | (2006.01) |
| A61K 31/5355 | (2006.01) |
| C07D 237/20 | (2006.01) |
| C07D 237/22 | (2006.01) |
| C07D 239/10 | (2006.01) |
| C07D 241/18 | (2006.01) |
| C07D 243/08 | (2006.01) |
| C07D 413/12 | (2006.01) |
| A61P 35/00 | (2006.01) |
| C07D 401/04 | (2006.01) |
| C07D 403/04 | (2006.01) |
| C07D 405/04 | (2006.01) |
| C07D 409/04 | (2006.01) |
| C07D 211/74 | (2006.01) |
| C07D 211/72 | (2006.01) |
| C07D 211/84 | (2006.01) |
| C07D 211/86 | (2006.01) |
| C07D 213/73 | (2006.01) |
| C07D 213/76 | (2006.01) |
| C07D 213/22 | (2006.01) |

(52) U.S. Cl. .................. 514/249; 514/250; 514/218; 514/234.2; 540/553; 540/575; 544/114; 544/238; 544/231; 544/258; 544/118; 546/257; 546/304

(58) Field of Classification Search ................ 544/258, 544/238, 231, 118; 514/252.01, 252.02, 514/252.03, 252.05, 249, 250, 218, 234.2; 540/575

See application file for complete search history.

(56) References Cited

FOREIGN PATENT DOCUMENTS

| WO | WO 01/19825 A1 | 3/2001 |
|---|---|---|
| WO | WO 03/020722 A1 | 3/2003 |
| WO | WO 2004/076454 A1 | 9/2004 |

OTHER PUBLICATIONS

Disorders Index of the National Institute of Neurological Disorders and Stroke, http://www.ninds.nih.gov/disorders/disorder_index.htm?css=print , 2006.*
Masuda, et al., Oncogene (2003) 22, 1012-1023.*
Ito, et al., Anticancer Research, 2004, Vo. 24, No. 1, pp. 259+ (Abstract).*
Mito, et al., Leuk. Lymphoma, Feb. 2005, 46(2): 225+ (PubMed abstract).*
Viral Defense Found., <http://www.viraldefense.org/mission.htm>, downloaded Jul. 10, 2007.*

(Continued)

*Primary Examiner*—Cecilia M. Jaisle
(74) *Attorney, Agent, or Firm*—Michael Morris; Mary-Ellen M. Devlin; Anthony P. Bottino

(57) ABSTRACT

Disclosed are new dihydropteridinones of general formula (I)

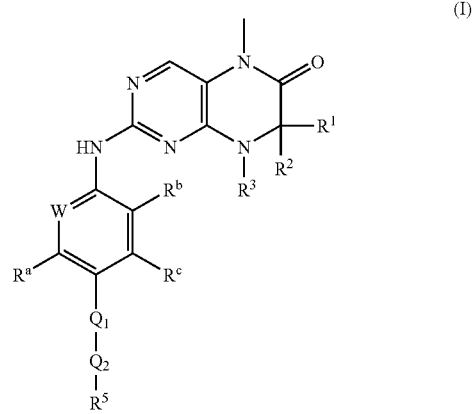

wherein the groups $R^1$ to $R^5$, $R^a$ to $R^c$, W, $Q_1$ and $Q_2$ have the meanings given in the claims and specification, the isomers thereof and the use thereof for preparing a pharmaceutical composition for the treatment of diseases characterised by excessive or abnormal cell proliferation.

10 Claims, No Drawings

OTHER PUBLICATIONS

Visiting Nurse Assns. of America, <http://www.vnaa.org/vnaa/gen/Germ_Protection_Center_Cold_and_Flu_Resources,html . . . >, downloaded May 16, 2007.*
Disorders Index of the National Institute of Neurological Disorders and Stroke, <http://www.ninds.nih.gov/disorders/disorder_index.htm?css=print >., downloaded Nov. 17, 2006.*
Blain, et al., J. of Biol. Chem., vol. 272,, No. 41, Oct. 10, 1997, 25863-25872.*
BBC News/Health, Killer Breast Cancer Therapy Hope, <http://newsvote.bbc.co.uk/mpapps/pagetooles/print/news.bbc.co.uk/1/hi/health/4619900.stm>, downloaded Jan. 31, 2007.*
Masuda, et al., Oncogene (Feb. 20, 2003) 22, 1012-1023.*
Verschuren, et al., J. Gen. Virology (2004), 85, 1347-1361.*
USPTO, Training Materials, 35 USC 112, 1st par., Enablement of Chem/Biotech Applns., <<http://www.uspto.gov/web/offices/pac/dapp/1pecba.htm#7>> Enablement Decision Tree, downloaded, Jul. 10, 2007.*
Printout from Leukemia & Lymphoma Society website, <http://www.leukemia-lymphoma.org/all_page?item_id=7026>; downloaded Jul. 12, 2007.*
Printout from Karolinska Institutet website, <http://www.mic.ki.se/Diseases/C14.html>, downloaded Jul. 12, 2007.*
Printout from National Kidney Found. website, <http://www.kidney.org/kidneydisease/ckd/index.cfm.>, downloaded Jul. 12, 2007.*
Leukemia & Lymphoma Society website, <http://www.leukemia-lymphoma.org/all_page?item_id=7030&viewmode=print>, downloaded Jul. 13, 2007.*
Printout from Medline Plus website, <http://www.nlm.nih.gov/medlineplus/print/bacterialinfections.html>, downloaded Jul. 13, 2007.*
Printout on viral infections from the Medline Plus website, <http://www.nlm.nih.gov/medlineplus/viralinfections.html>, downloaded Jul. 12, 2007.*

* cited by examiner

DIHYDROPTERIDINONES, PROCESSES FOR PREPARING THEM AND THEIR USE AS PHARMACEUTICAL COMPOSITIONS

APPLICATION DATA

This application claims benefit to European Patent Application no. EP 04 020 339.0 filed Aug. 27, 2004.

The present invention relates to new dihydropteridinones of general formula (1)

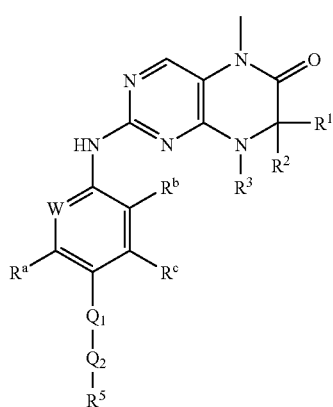

wherein the groups $R^1$ to $R^5$, $R^a$ to $R^c$, W, $Q_1$ and $Q_2$ have the meanings given in the claims and specification, the isomers thereof, processes for preparing these dihydropteridinones and their use as pharmaceutical compositions.

BACKGROUND TO THE INVENTION

Pteridinone derivatives are known from the prior art as active substances with an antiproliferative activity. WO 01/019825 and WO 03/020722 describe the use of pteridinone derivatives for the treatment of tumoral diseases.

Tumour cells wholly or partly elude regulation and control by the body and are characterised by uncontrolled growth. This is based on the one hand on the loss of control proteins, such as e.g. Rb, p16, p21 and p53 and also on the activation of so-called accelerators of the cell cycle, the cyclin-dependent kinases (CDK's).

In addition, the protein kinase Aurora B has been described as having an essential function during entry into mitosis. Aurora B phosphorylates histone H3 at Ser10 and thus initiates chromosome condensation (Hsu et al. 2000, *Cell* 102:279-91). A specific cell cycle arrest in the G2/M phase may however also be triggered e.g. by the inhibition of specific phosphatases such as e.g. Cdc25C (Russell and Nurse 1986, *Cell* 45:145-53). Yeasts with a defective Cdc25 gene arrest in the G2 phase, while overexpression of Cdc25 leads to premature entry into the mitosis phase (Russell and Nurse 1987, *Cell* 49:559-67). Moreover, an arrest in the G2/M phase may also be triggered by the inhibition of certain motor proteins, the so-called kinesins such as e.g. Eg5 (Mayer et al. 1999, *Science* 286:971-4), or by agents which stabilise or destabilise microtubules (e.g. colchicin, taxol, etoposide, vinblastin, vincristine) (Schiff and Horwitz 1980, *Proc Natl Acad Sci USA* 77:1561-5).

In addition to the cyclin-dependent and Aurora kinases the so-called polo-like kinases, a small family of serine/threonine kinases, play an important part in the regulation of the eukaryotic cell cycle. Hitherto, the polo-like kinases PLK-1, PLK-2, PLK-3 and PLK-4 have been described in the literature. PLK-1 in particular has been shown to play a central part in the regulation of the mitosis phase. PLK-1 is responsible for the maturation of the centrosomes, for the activation of phosphatase Cdc25C, and for the activation of the Anaphase Promoting Complex (Glover et al. 1998, *Genes Dev.* 12:3777-87; Qian et al. 2001, *Mol Biol Cell.* 12:1791-9). The injection of PLK-1 antibodies leads to a G2 arrest in untransformed cells, whereas tumour cells arrest in the mitosis phase (Lane and Nigg 1996, *J Cell Biol.* 135: 1701-13). Overexpression of PLK-1 has been demonstrated for various types of tumour, such as non-small-cell lung cancer, plate epithelial carcinoma, breast and colorectal carcinoma (Wolf et al. 1997, *Oncogene* 14:543-549; Knecht et al. 1999, *Cancer Res.* 59:2794-2797; Wolf et al. 2000, *Pathol. Res. Pract.* 196:753-759; Takahashi et al. 2003, *Cancer Sci.* 94:148-52). Therefore, this category of proteins also constitutes an interesting approach to therapeutic intervention in proliferative diseases (Liu and Erikson 2003, *Proc Natl Acad Sci USA* 100:5789-5794).

The resistance of many types of tumours calls for the development of new pharmaceutical compositions for combating tumours. The aim of the present invention is to provide new compounds having an antiproliferative activity.

DETAILED DESCRIPTION OF THE INVENTION

Surprisingly it has been found that compounds of general formula (I) wherein the groups $R^1$ to $R^5$, $R^a$ to $R^c$, W, $Q_1$ and $Q_2$ have the meanings given hereinafter act as inhibitors of specific cell cycle kinases, particularly the polo-like kinases. The compounds named have an antiproliferative activity, in that they arrest cells in the mitosis phase of the cell cycle before programmed cell death is initiated in the arrested cells. Thus, the compounds according to the invention may be used for example to treat diseases connected with the activity of specific cell cycle kinases and characterised by excessive or abnormal cell proliferation.

The present invention therefore relates to compounds of general formula (1)

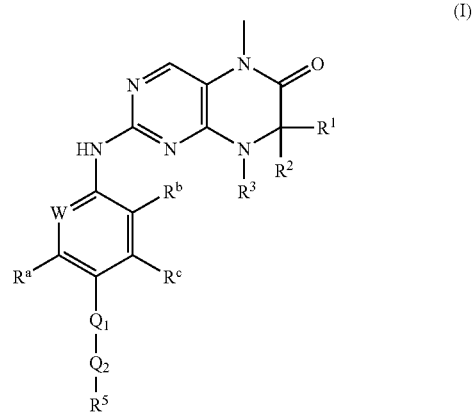

wherein
W denotes N or C—$R^4$,
$R^1$, $R^2$ each independently of one another denote hydrogen or optionally mono- or polysubstituted $C_{1-6}$alkyl, $C_{2-6}$alkenyl, $C_{2-6}$alkynyl, or $R^1$ and $R^2$ together form a saturated or partially unsaturated 2-5-membered alkyl bridge wherein a —CH$_2$- group may be replaced by O, S, —NR$^8$ or a —CH- group may be replaced by N;

R$^3$ denotes hydrogen or a group selected from among optionally mono- or polysubstituted C$_{1-2}$alkyl, C$_{2-12}$ alkenyl, C$_{2-12}$-alkynyl, cycloalkyl, aryl, heteroaryl and heterocyclyl, while the substituent(s) may be identical or different and are selected from among halogen, —NO$_2$, —OR$^8$, —C(=O)R$^8$, —C(=O)OR$^8$, —C(=O)NR$^8$R$^9$, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen, or R$^1$ and R$^3$ or R$^2$ and R$^3$ together form a saturated or partially unsaturated 2-5-membered alkyl bridge, wherein a —CH$_2$- group may be replaced by O, S, —NR$^8$ or a —CH— group may be replaced by N;

R$^4$ denotes a group selected from among hydrogen, —CN, hydroxy, halogen, —OR$^8$ and —NR$^6$R$^7$, or a group selected from among optionally mono- or polysubstituted C$_{1-6}$alkyl, C$_{2-6}$alkenyl, C$_{2-6}$alkynyl, C$_{1-5}$alkyloxy, C$_{2-5}$alkenyloxy, C$_{2-5}$alkynyloxy, C$_{1-6}$alkylthio, C$_{1-6}$alkylsulphoxo and C$_{1-6}$alkylsulphonyl, while the substituent(s) may be identical or different and are selected from among halogen, —NO$_2$, —OR$^8$, —C(=O)R$^8$, —C(=O)OR$^8$, —C(=O)NR$^8$R$^9$, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$—NR$^8$SO$_2$NR$^9$R$^{10}$, —OSO$_2$NR$^8$R$^9$ and pseudohalogen;

Q$_1$ denotes a group selected from among optionally mono- or polysubstituted piperidinyl, piperazinyl, homopiperazinyl, pyrrolidinyl, tropenyl, azacycloheptyl and —N(R$^8$)—(CH$_2$)$_n$—; while the substituent(s) may be identical or different and are selected from among halogen, —NO$_2$, R$^8$, —OR$^8$, —C(=O)R$^8$, —C(=O)OR$^8$, —C(=O)NR$^8$R$^9$, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen;

Q$_2$ is either absent or denotes a group selected from among optionally mono- or polysubstituted C$_{1-16}$alkylene, C$_{2-16}$alkenylene, C$_{2-16}$alkynylene, cycloalkyl, aryl, heterocyclyl and heteroaryl, while the substituent(s) may be identical or different and are selected from among halogen, —NO$_2$, R$^8$, —OR$^8$, —C(=O)R$^8$, —C(=O)OR$^8$, —C(=O)NR$^8$R$^9$, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$—NR$^8$SO$_2$NR$^9$R$^{10}$, —OSO$_2$NR$^8$R$^9$ and pseudohalogen;

R$^5$ denotes hydrogen or a group selected from among optionally mono- or polysubstituted C$_{1-16}$alkyl, C$_{2-16}$alkenyl, C$_{2-16}$alkynyl, cycloalkyl, aryl, heteroaryl and heteroaryl, while the substituent(s) may be identical or different and are selected from among halogen, —NO$_2$, R$^8$, —OR$^8$, —C(=O)R$^8$, —C(=O)OR$^8$, —C(=O)NR$^8$R$^9$, —NR$^8$R$^9$, —NR$^8$COR$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen;

R$^a$, R$^b$, R$^c$, each independently of one another denote a group selected from among hydrogen, halogen, —NO$_2$, —OR$^8$, —C(=O)R$^8$, —C(=O)OR$^8$, —C(=O)NR$^8$R$^9$, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen;

or an optionally mono- or polysubstituted group selected from among C$_{1-6}$alkyl, C$_{2-6}$alkenyl, C$_{2-6}$alkynyl, C$_{3-6}$cycloalkyl, aryl, heterocyclyl and heteroaryl, while the substituents may be identical or different and are selected from among halogen, —NO$_2$, —OR$^8$, —C(=O)R$^8$, —C(=O)OR$^8$, —C(=O)NR$^8$R$^9$, —NR$^8$R$^9$, —NR$^8$COR$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen;

R$^6$, R$^7$ each independently of one another denote hydrogen or a group selected from among optionally mono- or polysubstituted C$_{1-16}$alkyl, C$_{2-16}$alkenyl, C$_{2-16}$alkynyl, cycloalkyl, aryl, heterocyclyl and heteroaryl while the substituent(s) may be identical or different and are selected from among halogen, —NO$_2$, —OR$^8$, —C(=O)R$^8$, —C(=O)OR$^8$, —C(=O)NR$^8$R, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen;

R$^8$, R$^9$ and R$^{10}$ each independently of one another denote hydrogen or a group selected from among optionally substituted C$_{1-8}$alkyl, C$_{2-8}$alkenyl, C$_{2-8}$alkynyl, cycloalkyl, aryl, heterocyclyl and heteroaryl, while the substituent(s) may be identical or different and are selected from among halogen, methyl, ethyl, amino, methylamino, dimethylamino, —OH and pseudohalogen;

n denotes 0, 1, 2 or 3 optionally in the form of the tautomers, racemates, enantiomers, diastereomers and mixtures thereof, and optionally the pharmacologically acceptable acid addition salts thereof.

In one aspect the invention relates to compounds of general formula (1), wherein W denotes C—R$^4$.

In another aspect the invention relates to compounds of general formula (1), wherein R$^b$ denotes a group selected from among hydrogen, —F, —Cl, methyl and ethyl.

In another aspect the invention relates to compounds of general formula (1), wherein R$^a$ and R$^c$ each independently of one another denote hydrogen or fluorine; or an optionally mono- or polysubstituted group selected from among C$_{1-2}$alkyl, C$_2$alkenyl, C$_2$alkynyl, C$_{3-6}$cycloalkyl, aryl, heterocyclyl and heteroaryl, while the substituents may be identical or different and are selected from among hydrogen, halogen, —NO$_2$, —OR$^8$, —C(=O)R$^8$, —C(=O)OR$^8$, —C(=O)NR$^8$R$^9$, —NR$^8$R$^9$, —NR$^8$C(=O)R$^9$, —NR$^8$C(=O)OR$^9$, —NR$^8$C(=O)NR$^9$R$^{10}$, —NR$^8$C(=O)ONR$^9$R$^{10}$, —NR$^8$SO$_2$R$^9$, —N=CR$^8$R$^9$, —SR$^8$, —SOR$^8$, —SO$_2$R$^8$, —SO$_2$NR$^8$R$^9$, —NR$^8$SO$_2$NR$^9$R$^{10}$, —OSO$_2$NR$^8$R$^9$ and pseudohalogen.

In an additional aspect the invention relates to compounds of general formula (1), wherein R$^a$ and R$^c$ each independently of one another denote hydrogen or fluorine.

In an essential aspect the invention relates to compounds of general formula (1), wherein $R^1$ and $R^2$ each independently of one another denote hydrogen or optionally substituted $C_{1-3}$alkyl, $C_{2-3}$alkenyl, $C_{2-3}$-alkynyl, or $R^1$ and $R^2$ together form a saturated or partially unsaturated 2-5-membered alkyl bridge, wherein a —$CH_2$- group may be replaced by O, S, —$NR^8$ or a —CH— group may be replaced by N.

The invention also relates to compounds of general formula (1), wherein $R^5$ denotes hydrogen, methyl, ethyl, hydroxy, methoxy, ethoxy, amino, methylamino, dimethylamino, F, Cl, Br, O-propargyl, CN, methylthio, $CONH_2$, ethynyl, propynyl, butynyl or allyl.

The invention also encompasses compounds of general formula (1) wherein $Q_1$ denotes piperazinyl or homopiperazinyl.

In one aspect the invention relates to the use of compounds of general formula (1) as pharmaceutical compositions.

In another aspect the invention relates to the use of compounds of general formula (1) as pharmaceutical compositions with an antiproliferative activity.

In another aspect the invention relates to the use of compounds of general formula (1) for preparing a pharmaceutical composition for the treatment and/or prevention of diseases selected from among cancer, bacterial and viral infections, inflammatory and autoimmune diseases, chemotherapy-induced alopecia and mucositis, cardiovascular diseases, nephrological diseases, as well as chronic and acute neurodegenerative diseases.

In an additional aspect the invention relates to the use of compounds of general formula (1) for preparing a pharmaceutical composition for inhibiting the polo-like kinases.

In an essential aspect the invention relates to the use of compounds of general formula (1) for preparing a pharmaceutical composition for inhibiting the polo-like kinases PLK1.

In an important aspect the invention relates to the use of a compound of formula (1) for preparing a pharmaceutical composition for the treatment and/or prevention of tumoral diseases based on overexpression of the polo-like kinases.

In one aspect the invention relates to a method for the treatment and/or prevention of diseases selected from among cancer, bacterial and viral infections, inflammatory and autoimmune diseases, chemotherapy-induced alopecia and mucositis, cardiovascular diseases, nephrological diseases, as well as chronic and acute neurodegenerative diseases, characterised in that an effective amount of a compound of formula (I) is administered to a patient.

The invention also relates to pharmaceutical preparations containing as active substance one or more compounds of general formula (I), optionally in conjunction with conventional excipients and/or carriers.

Definitions

As used herein, the following definitions apply, unless stated otherwise.

By alkyl substituents are meant in each case saturated, straight-chain or branched aliphatic hydrocarbon groups (alkyl group).

The alkenyl substituents are in each case straight-chain or branched, unsaturated alkyl groups which have at least one double bond.

By alkynyl substituents are meant in each case straight-chain or branched, unsaturated alkyl groups which have at least one triple bond.

Haloalkyl refers to alkyl groups wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CHFCH_2CH_3$ and —$CHFCH_2CF_3$.

Halogen relates to fluorine, chlorine, bromine and/or iodine atoms.

By pseudohalogen are meant the following groups: —OCN, —SCN, —$CF_3$ and —CN.

By cycloalkyl is meant a mono- or bicyclic ring, while the ring system may be a saturated ring or an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl, norbornenyl, spiro[5.5]undecane, spiro[5.4]decane and spiro[4.4]nonane.

Aryl relates to monocyclic or bicyclic rings with 6-12 carbon atoms such as for example phenyl and naphthyl.

By heteroaryl are meant mono- or bicyclic rings which contain instead of one or more carbon atoms one or more identical or different heteroatoms, such as e.g. nitrogen, sulphur or oxygen atoms. Examples include fuiryl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, cumarinyl, isocumarinyl, chromonyl, chromanonyl, pyridinyl-N-oxide tetrahydroquinolinyl, dihydroquinolinyl, dihydroquinolinonyl, dihydroisoquinolinonyl, dihydrocumarinyl, dihydroisocumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-5-oxide and benzothiopyranyl-S,S-dioxide.

Heterocyclyl relates to saturated or unsaturated, non-aromatic mono-, bicyclic or bridged bicyclic rings comprising 5-12 carbon atoms, which carry heteroatoms, such as nitrogen, oxygen or sulphur, instead of one or more carbon atoms. Examples of such heterocyclyl groups are tetrahydrofuranyl, pyrrolidinyl, pyrrolinyl, imidazolidinyl, imidazolinyl, pyrazolidinyl, pyrazolinyl, piperidyl, piperazinyl, indolinyl, isoindoliny, morpholinyl, thiomorpholinyl, homomorpholinyl, homopiperidyl, homopiperazinyl, thiomorpholinyl-S-oxide, thiomorpholinyl-S,S-dioxide, pyrrolidinyl, pyrrolinyl, tetrahydropyranyl, piperidinyl, tetrahydrofuranyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-5-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane, 2,7-diaza-spiro[3.5]nonane, 2,7-diaza-spiro[4.4]nonane, 2,8-diaza-spiro[4.5]decane and 3,9-diaza-spiro[5.5]undecane.

The Examples that follow illustrate the present invention without restricting its scope:

Preparation of the Compounds According to the Invention:

Analysis

Preparative Chromatography:

For medium pressure chromatography (MPLC) silica gel made by Millipore (name: Granula Silica Si-60A 35-70 μm) or C-18 RP-silica gel made by Macherey Nagel (name: Polygoprep 100-50 C18) is used.

For preparative high pressure chromatography columns made by Waters (name: XTerra Prep. MS C18, 5 μM, 30*100 mm or Symmetrie C18, 5 μm, 19*100) are used.

Nuclear Magnetic Resonance (NMR) Spectroscoyv:

The measurement is carried out in deuterised dimethylsulphoxide-d6. If other solvents are used they are explicitly mentioned in the Examples or in the methods. The measurements are given on a delta scale in ppm. Tetramethylsilane is taken as the standard. The measurements are carried out on an Avance 400 (400 MHz NMR spectrometer) made by Messrs Bruker Biospin GmbH.

Mass Spectroscopy/UV Spectrometer:

These data are generated using an HPLC-MS apparatus (high performance liquid chromatography with mass detector) made by Agilent.

The apparatus is constructed so that a diode array detector (G1315B made by Agilent) and a mass detector (1100 LS-MSD SL; G1946D; Agilent) are connected in series downstream of the chromatography apparatus (column: Zorbax SB-C8, 3.5 μm, 2,1*50, Messrs. Agilent). The apparatus is operated with a flow of 0.6 ml/min. For a separation process a gradient is run through within 3.5 min (start of gradient: 95% water and 5% acetonitrile; end of gradient: 5% water and 95% acetonitrile; in each case 0.1% formic acid is added to the two solvents).

The compounds according to the invention may be prepared according to methods of synthesis A to C described hereinafter, wherein the substituents of general formulae (I to VI) have the meanings given hereinbefore. These methods are to be understood as being an illustration of the invention without restricting it to their content.

Method A

Step 1A

The intermediate compound III is prepared by substitution of a leaving group LG, for example halogen, SCN, methoxy, preferably chlorine or fluorine, on an aromatic system I by a nucleophile II.

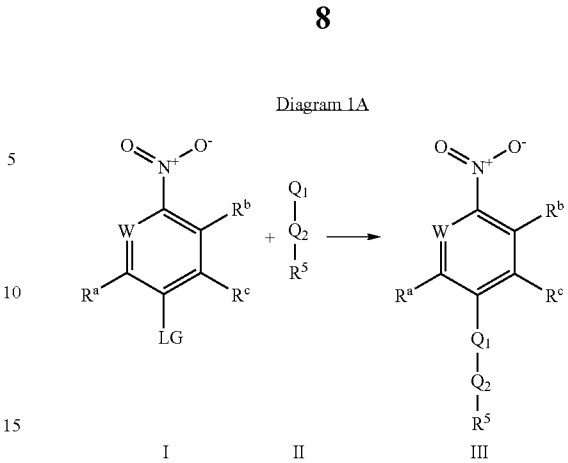

Diagram 1A 1 equivalent of the compound I and 1 to 1.5 equivalents of the compound H are stirred in a solvent, for example 1,4-dioxane, tetrahydrofuran, N,N-dimethylformamide, N-methyl-2-pyrrolidinone or N,N-dimethylacetamide.

At a temperature of 15 to 25° C., 1 to 2.5 equivalents of a base such as potassium carbonate, sodium carbonate, caesium carbonate, N-ethyl-N,N-diisopropylamine or triethylamine are added. The reaction mixture is stirred for a further 12 to 72 h at a temperature of 50 to 100° C. Then the solvent is distilled off and the residue is purified by chromatography.

Step 2A

The intermediate compound IV is prepared by reduction of the nitro group to an amino function.

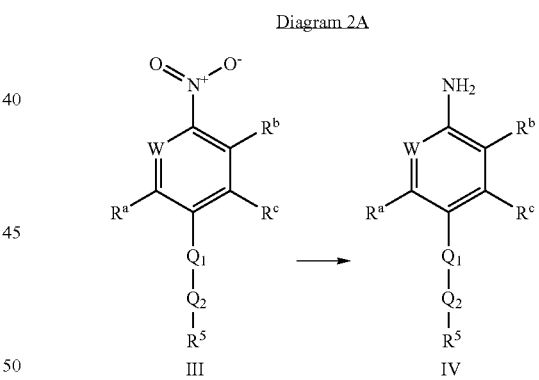

Diagram 2A

The compound III is dissolved in a solvent, for example methanol, ethanol, ethyl acetate, tetrahydrofuran or acetone. A catalyst, for example palladium on charcoal, palladium hydroxide or Raney nickel is added. This suspension is transferred into an autoclave. This is acted upon with a hydrogen pressure of 2 to 10 bar. The mixture is stirred for 1 to 10 days at 20-40° C. Then the catalyst is filtered off and the solvent is eliminated in vacuo.

Step 3A

The end compound VI is prepared by substitution of a leaving group LG, for example halogen, SCN, methoxy, preferably chlorine, on a heteroaromatic system V by a nucleophile IV.

Diagram 3A

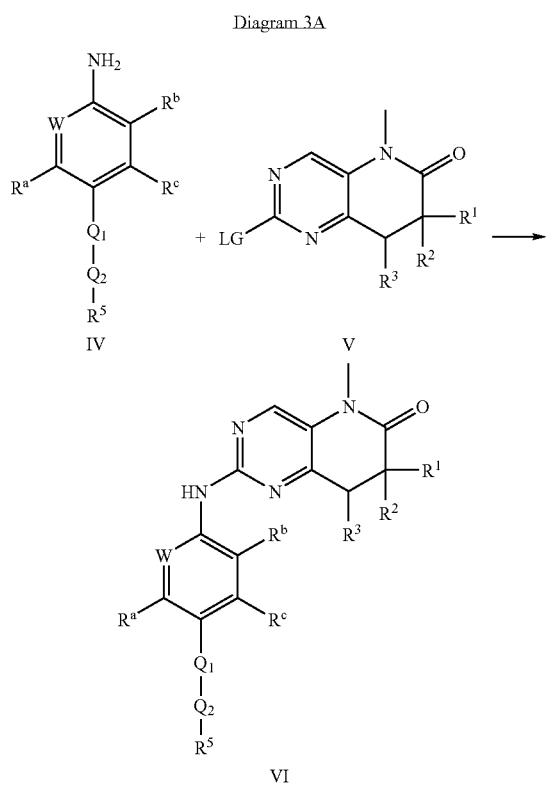

1 equivalent of the compound V (WO 03/020722) and 1 to 3 equivalents of the compound IV are stirred in a solvent, for example 1,4-dioxane, N,N-dimethylformamide, N,N-dimethylacetamide, ethanol, methanol, water or N-methyl-2-pyrrolidinone.

At a temperature of 15 to 40° C., 0.1 to 2 equivalents of an inorganic acid, for example sulphuric acid or hydrochloric acid, are added. The reaction mixture is stirred for a further 1 to 48 h at a temperature of 50 to 120° C. Then the solvent is distilled off and the residue is purified by chromatography.

Method 1

2-methoxy-4-(4-pyrrolidin-1-yl-piperidin-1-yl)-phenylamine

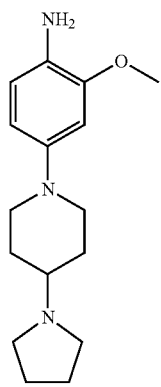

a) 4-fluoro-2-methoxy-1-nitro-benzene 20 g (126 mmol) 5-fluoro-2-nitro-phenol are dissolved in 300 ml acetone. 22.6 g (163 mmol) potassium carbonate are added and the mixture is stirred for 30 min at 20° C. Over a period of 10 min, 9.4 ml (150 mmol) methyl iodide, diluted in 50 ml acetone, is added and the mixture is stirred for a further 18 h at 20° C. Then it is left for another 12 h at 65° C. with stirring. The solvent is eliminated in vacuo, the residue is taken up in water and extracted three times with ethyl acetate. Then the combined organic phases are extracted three times with 10% aqueous sodium carbonate solution. The organic phase is dried over magnesium sulphate. The solvent is eliminated in vacuo.

Yield: 21.1 g (123 mmol; 98%)

UV max: 230/266/322 nm.

b) 1-(3-methoxy-4-nitro-phenyl)-4-pyrrolidin-1-yl-piperidine 200 mg (1.170 mmol) 4-fluoro-2-methoxy-1-nitro-benzene are dissolvedjin 1 ml NMP, combined with 198 mg (1.284 mmol) 4-pyrrolidin-1-yl-piperidine and 300 µl diisopropylethylamine and stirred for 17 h at 80° C. Then the solvent is eliminated in vacuo. The crude product is purified by column chromatography. The carrier material used is C18-RP gel and a gradient is run through which consists of 95% water and 5% acetonitrile at the starting point and 5% water and 95% acetonitrile at the finishing point.

Yield: 321 mg (1.053 mmol; 90%)

UV max: 398 nm

MS (ESI): 306 $(M+H)^+$.

c) 2-methoxy-4-(4-pyrrolidin-1-yl-piperidin-1-yl)-phenylamine 321 mg (1.053 mmol) 1-(3-methoxy-4-nitro-phenyl)-4-pyrrolidin-1-yl-piperidine are dissolved in 10 ml THF, combined with 30 mg Raney nickel and then shaken for 9 days at 20° C. under 4 bar hydrogen atmosphere. The catalyst is filtered off and washed again with THF. The solvent is eliminated in vacuo.

Yield: 269 mg (0.980 mmol; 93%)

UV max: 250/286 nm

MS (ESI): 276 $(M+H)^+$.

The following compounds are prepared analogously to this process:

| | MS (ESI) $(M + H)^+$: |
|---|---|
| 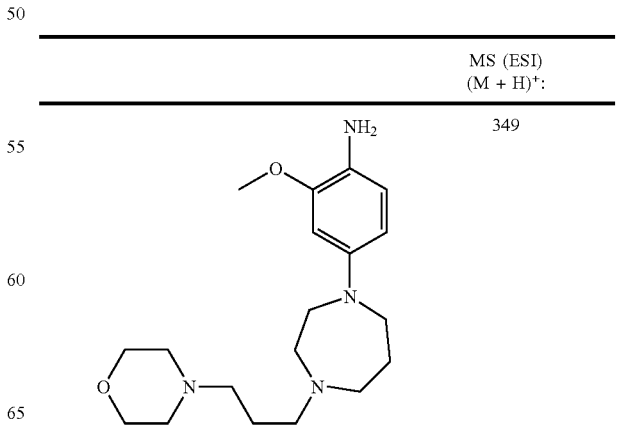 | 349 |

| -continued | MS (ESI) (M + H)+: |
|---|---|
| 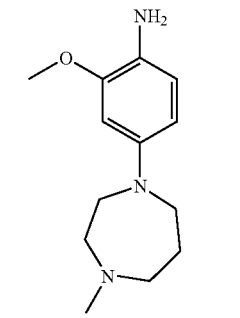 | 236 |
| 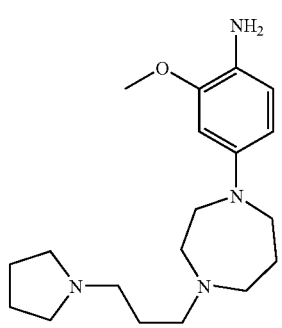 | 333 |
| 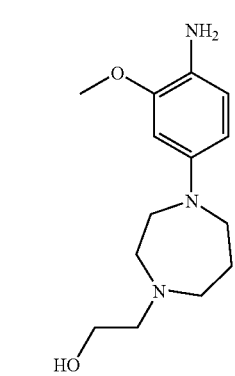 | 266 |
| 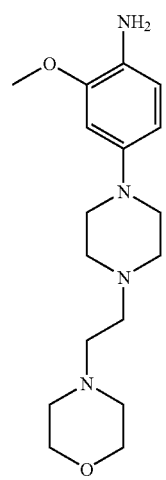 | 321 |
| -continued | MS (ESI) (M + H)+: |
|---|---|
| 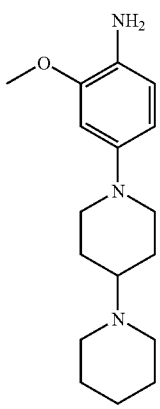 | 290 |
| 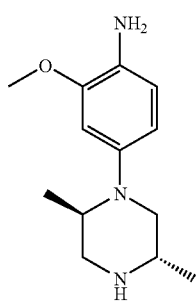 | 236 |
| 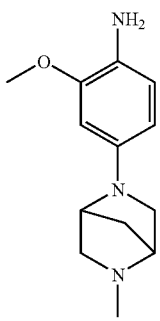 | 234 |
| 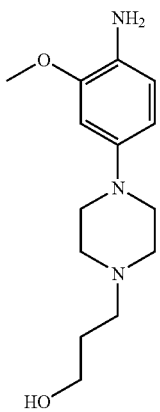 | 266 |

| | MS (ESI) (M + H)+: |
|---|---|
| 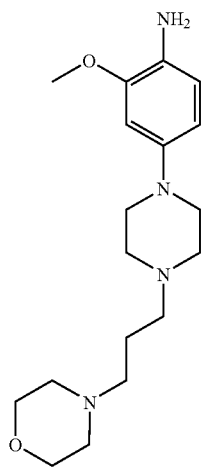 | 335 |
| 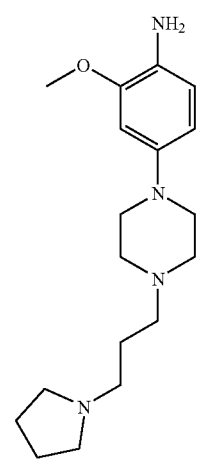 | 319 |
| 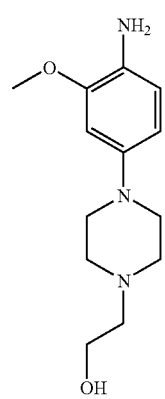 | 252 |
| | MS (ESI) (M + H)+: |
|---|---|
| 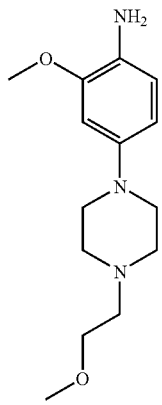 | 266 |
| 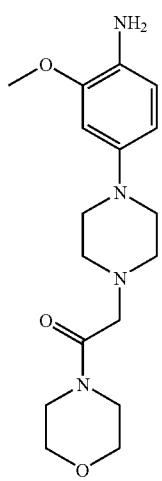 | 335 |
| 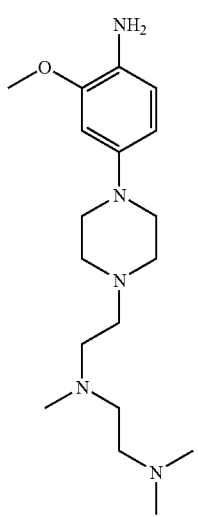 | 336 |

| | MS (ESI) (M + H)+: |
|---|---|
| 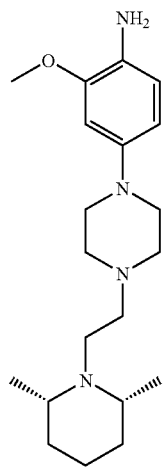 | 347 |
| | 319 |
| 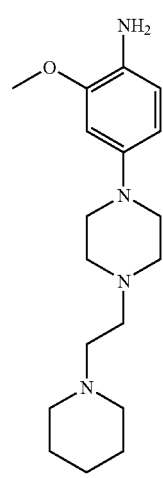 | 305 |
| | MS (ESI) (M + H)+: |
|---|---|
| 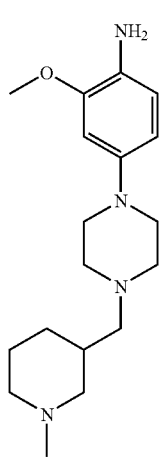 | 319 |
| | 319 |
| 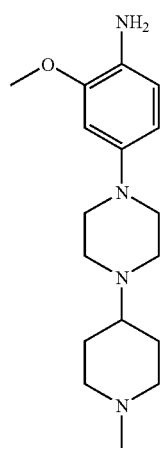 | 305 |

-continued
| | MS (ESI) (M + H)+: |
|---|---|
| 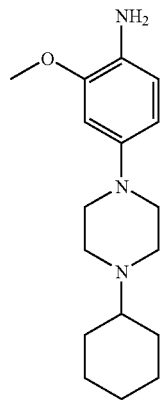 | 290 |
| 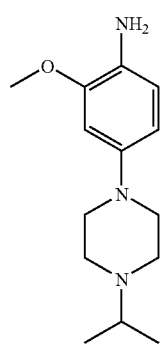 | 250 |
| 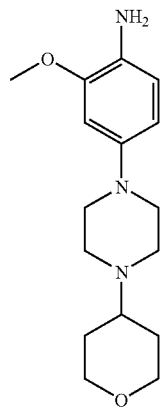 | 292 |
| 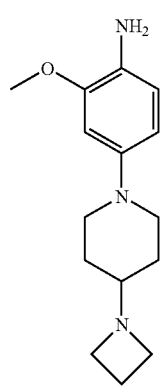 | 262 |
-continued
| | MS (ESI) (M + H)+: |
|---|---|
| 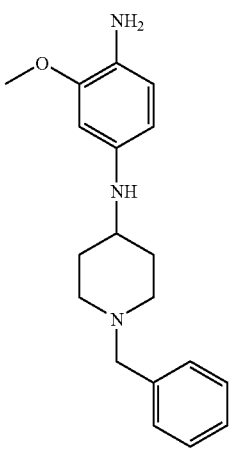 | 312 |
| 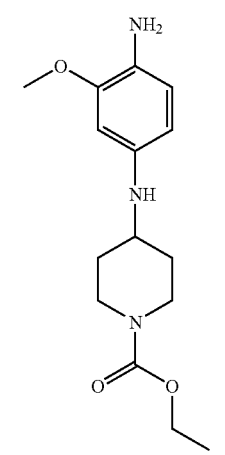 | 294 |
| 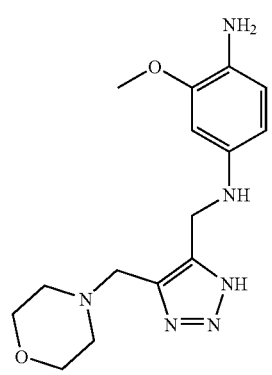 | 319 |

| | MS (ESI) (M + H)+: |
|---|---|
| 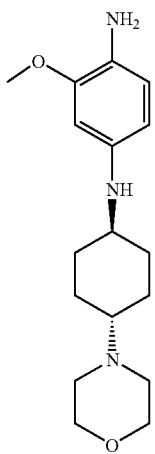 | 306 |
| 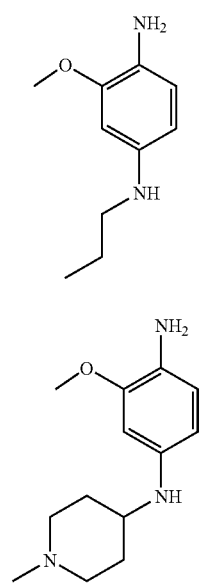 | 222 |
| | 181 |
| | 236 |

| | MS (ESI) (M + H)+: |
|---|---|
| 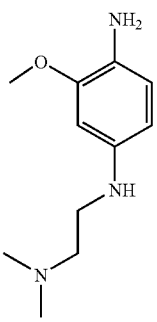 | 210 |
| 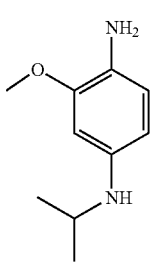 | 181 |

EXAMPLE 1

(R)-7-ethyl-8-isopropyl-2-[2-methoxy-4-(4-pyrrolidin-1-yl-piperidin-1-yl)-phenylamino]-5-methyl-7,8-dihydro-5H-pteridin-6-one

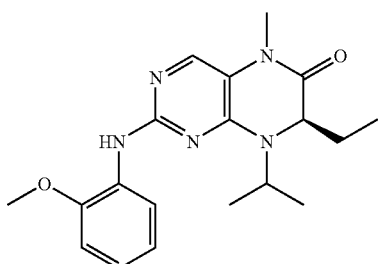

50 mg (0.186 mmol) (R)-2-chloro-7-ethyl-8-isopropyl-5-methyl-7,8-dihydro-5H-pteridin-6-one are dissolved in 0.5 ml of ethanol and 1 ml distilled water, combined with 136 μl of a 33% aqueous hydrochloric acid and 56 mg (0.203 mmol) 2-methoxy-4-(4-pyrrolidin-1-yl-piperidin-1-yl)-phenylamine (method 1) and stirred for 3 h at 100° C.

Then the solvent is eliminated in vacuo. The crude product is purified by column chromatography. The carrier material used is C 18-RP gel and a gradient is run through which consists of 95% water and 5% acetonitrile at the starting point and 5% water and 95% acetonitrile at the finishing point.

Yield: 37 mg (0.060 mmol; 32%)
UV max: 286 nm
MS (ESI): 508 (M+H)+
¹H-NMR: 0.72-0.79 (m, 3H), 1.25-1.37 (m, 6H), 1.76-2.04 (m, 8H), 2.10-2.22 (m, 2H), 2.73-2.84 (m, 2H), 3.01-3.11 (m, 2H), 3.19 (s, 3H), 3.81 (s, 3H), 3.84-3.92 (m, 2H), 4.23-4.31 (m, 1H), 4.44-4.49 (m, 1H), 6.62-6.86 (m, 2H), 7.37-7.65 (m, 2H), 9.49 (sb, 1H), 11.07 (sb, 1H).

EXAMPLES 2-35

The following compounds are prepared by an analogous process to the one described in Example 1. (R)-2-chloro-7-ethyl-8-isopropyl-5-methyl-7,8-dihydro-5H-pteridin-6-one and a corresponding aniline derivative (method 1) are used.

| # | R: | UV max [nm]: | MS(ESI) (M + H)+: | NMR: |
|---|---|---|---|---|
| 2 | | 230 | 581 | 0.70-0.80(m, 3H), 1.32(s, 6H), 1.75-2.00(m, 2H), 2.14-2.33(m, 3H), 2.99-3.14(m, 3H), 3.14-3.36(m, 8H), 3.36-3.58(m, 6H), 3.81-4.02(m, 9H), 4.26(s, 1H), 4.42-4.50(m, 1H), 6.36-6.43(m, 1H), 6.46(s, 1H), 7.34(s, 1H), 7.57(s, 1H), 9.49(s, 1H), 11.29 (s, 1H), 11.48(s, 1H) |
| 3 | | 226 | 468 | 0.71-0.80(m, 3H), 1.32(s, 6H), 1.75-1.87(m, 1H), 1.87-1.98(m, 1H), 2.12-2.23(m, 1H), 2.26-2.40(m, 1H), 2.74-2.85(m, 3H), 3.02-3.23(m, 5H), 3.71-3.92(m, 5H), 4.26(s, 1H), 4.43-4.51(m, 1H), 6.35-6.42(m, 1H), 6.44(s, 1H), 7.20-7.42(m, 1H), 7.54(s, 1H), 9.47(s, 1H), 10.98(s, 1H) |
| 4 | | 226; 286 | 565 | 0.69-0.83(m, 3H), 1.32(s, 6H), 1.74-2.06(m, 6H).2.11-2.29(m, 3H), 2.35-2.47(m, 1H), 2.92-3.03(m, 2H), 3.03-3.13(m, 1H), 3.13-3.26(m, 6H), 3.26-3.34(m, 2H), 3.43-3.58(m, 6H), 3.80-3.96(m, 6H), 4.26(s, 1H), 4.42-4.50(m, 1H), 6.36-6.43(m, 1H), 6.46(s, 1H), 7.34(s, 1H), 7.58(s, 1H), 9.50(s, 1H), 11.12(s, 1H), 11.30(s, 1H) |

-continued

| # | R: | UV max [nm]: | MS(ESI) (M + H)⁺: | NMR: |
|---|---|---|---|---|
| 5 | (2-methoxy-4-(4-(2-hydroxyethyl)-1,4-diazepan-1-yl)phenyl)amino- | 230 | 498 | 0.67-0.82(m, 3H), 1.31(s, 6H), 1.74-1.87(m, 1H), 1.87-1.98(m, 1H), 2.13-2.25(m, 1H), 2.33-2.45(m, 1H), 3.03-3.31(m, 7H), 3.42-3.60(m, 5H), 4.25(s, 1H), 4.42-4.53(m, 1H), 6.35-6.43(m, 1H), 6.45(s, 1H), 7.34 (s, 1H), 7.43-7.75(m, 1H), 9.49 (s, 1H), 10.70(s, 1H) |
| 6 | (2-methoxy-4-(4-(2-morpholinoethyl)piperazin-1-yl)phenyl)amino- | 286 | 553 | 0.72-0.78(m, 3H), 1.25-1.35 (m, 6H), 1.77-1.87(m, 1H), 1.88-1.97(m, 1H), 4.20-4.30 (m, 1H), 4.45-4.49(m, 1H), 6.61-6.66(m, 1H), 6.75-6.79 (m, 1H), 7.44-7.56(m, 1H), 7.59-7.70(m, 1H), 9.54(m, 1H) |
| 7 | (2-methoxy-4-(4-(piperidin-1-yl)piperidin-1-yl)phenyl)amino- | 286 | 522 | 0.69-0.79(m, 3H), 1.24-1.69 (m, 15H), 1.71-1.84(m, 3H), 2.27-2.37(m, 1H), 2.53-2.63 (m, 2H), 3.21(s, 3H), 3.59-3.70 (m, 2H), 3.82(s, 3H), 4.19-4.26 (m, 1H), 4.42-4.54(m, 1H), 6.42-4.49(m, 1H), 6.57-6.63 (m, 1H), 7.25(s, 1H), 7.72(s, 1H), 7.92-7.99(m, 1H) |

-continued
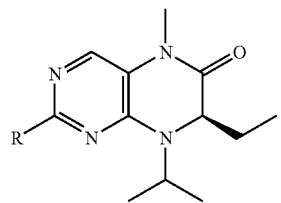
| # | R: | UV max [nm]: | MS(ESI) (M + H)+: | NMR: |
|---|---|---|---|---|
| 8 | (4-(2,5-dimethylpiperazin-1-yl)-2-methoxyphenyl)-NH-X₁ | 282 | 468 | 0.70-0.77(m, 3H), 0.95-1.01 (m, 3H), 1.21-1.33(m, 9H), 1.77-1.86(m, 1H), 1.88-1.97 (m, 1H), 2.83-2.93 (m, 1H), 3.00-3.09(m, 1H), 3.20(s, 3H), 3.82(s, 3H), 4.15-4.25(m, 1H), 4.45-4.49(m, 1H), 6.75-6.81 (m, 1H), 6.83-6.89(m, 1H), 7.55(m, 1H), 7.65-7.70(m, 1H), 9.42(sb, 1H), 9.48-9.60 (m, 2H) |
| 9 | (4-(5-methyl-2,5-diazabicyclo[2.2.1]heptan-2-yl)-2-methoxyphenyl)-NH-X₁ | 286 | 466 | 0.72-0.78(m, 3H), 1.24-1.33 (m, 6H), 1.57-1.68(m, 1H), 1.71-1.81(m, 2H), 1.86-1.92 (m, 1H), 2.30(s, 3H), 2.57-2.62 (m, 1H), 2.78-2.83(m, 1H), 3.15-3.22(m, 4H), 3.80(s, 3H), 4.17-4.23(m, 1H), 4.26-4.31 (m, 1H), 4.39-4.48(m, 1H), 6.09-6.15(m, 1H), 6.21-6.25 (m, 1H), 7.19(s, 1H), 7.69(s, 1H), 7.75-7.80(m, 1H) |
| 10 | (4-(4-(3-hydroxypropyl)piperazin-1-yl)-2-methoxyphenyl)-NH-X₁ | 286 | 498 | 0.72-0.78(m, 3H), 1.26-1.35 (m, 6H), 1.76-1.97(m, 4H), 3.04-3.22(m, 9H), 3.49-3.54 (m, 2H), 6.55-3.63(m, 2H), 3.82(s, 3H), 3.85-3.91(m, 2H), 4.22-4.31(m, 1H), 4.44-4.49 (m, 1H), 6.59-6.64(m, 1H), 6.73-6.77(m, 1H), 7.42-7.49 (m, 1H), 7.53-7.62(m, 1H), 9.44(sb, 1H), 10.66(sb, 1H) |

-continued
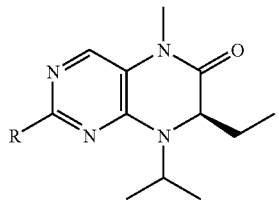
| # | R: | UV max [nm]: | MS(ESI) (M + H)+: | NMR: |
|---|---|---|---|---|
| 11 | HN-X₁ with 2-methoxy-4-(4-(3-morpholinopropyl)piperazin-1-yl)phenyl | 282 | 567 | 0.72-0.78(m, 3H), 1.25-1.35 (m, 6H), 1.77-1.97(m, 2H), 2.24-2.33(m, 2H), 3.56-3.65 (m, 2H), 3.79-4.03(m, 9H), 4.21-4.30(m, 1H), 4.45-4.49 (m, 1H), 6.60-6.65(m, 1H), 6.74-6.77(m, 1H), 7.42-7.50 (m, 1H), 7.54-7.66(m, 1H), 9.50(sb, 1H), 11.22-11.38(m, 2H) |
| 12 | HN-X₁ with 2-methoxy-4-(4-(3-(pyrrolidin-1-yl)propyl)piperazin-1-yl)phenyl | 282 | 551 | 0.72-0.79(m, 3H), 1.25-1.35 (m, 6H), 1.77-2.07(m, 6H), 2.19-2.28(m, 2H), 2.95-3.05 (m, 2H), 3.52-3.63(m, 4H), 3.82(s, 3H), 3.85-3.94(m, 2H), 4.21-4.30(m, 1H), 4.44-4.49 (m, 1H), 6.60-6.65(m, 1H), 6.73-6.78(m, 1H), 7.42-7.50 (m, 1H), 7.55-7.65(m, 1H), 9.49(sb, 1H), 10.85(sb, 1H), 11.22(sb, 1H) |

-continued

| # | R: | UV max [nm]: | MS(ESI) (M + H)+: | NMR: |
|---|---|---|---|---|
| 13 | (2-methoxy-4-(4-(2-hydroxyethyl)piperazin-1-yl)phenyl)amino-X₁ | 286 | 484 | 0.72-0.78(m, 3H), 1.26-1.35 (m, 6H), 1.76-1.97(m, 2H), 3.58-3.65(m, 2H), 3.80-3.92 (m, 7H), 4.22-4.30(m, 1H), 4.45-4.49(m, 1H), 6.58-6.63 (m, 1H), 6.72-6.76(m, 1H), 7.41-7.64(m, 2H), 9.46(sb, 1H), 10.47(sb, 1H) |
| 14 | (2-methoxy-4-(4-(2-methoxyethyl)piperazin-1-yl)phenyl)amino-X₁ | 286 | 498 | 0.72-0.79(m, 3H), 1.25-1.35 (m, 6H), 1.77-1.86(m, 1H), 1.88-1.97(m, 1H), 3.14-3.25 (m, 7H), 3.54-3.62(m, 2H), 3.76-3.91(m, 7H), 4.21-4.30 (m, 1H), 4.44-4.49(m, 1H), 6.58-6.63(m, 1H), 6.72-6.76 (m, 1H), 7.41-7.47(m, 1H), 7.56-7.65(m, 1H), 9.51(sb, 1H), 10.94(sb, 1H) |
| 15 | (2-methoxy-4-(4-(2-morpholino-2-oxoethyl)piperazin-1-yl)phenyl)amino-X₁ | 286 | 567 | 0.72-0.79(m, 3H), 1.27-1.34 (m, 6H), 1.77-1.97(m, 2H), 3.19(s, 3H), 3.50-3.67(m, 8H), 3.79-3.90(m, 5H), 4.23-4.30 (m, 1H), 4.40-4.49(m, 3H), 6.58-6.63(m, 1H), 6.72-6.76 (m, 1H), 7.45-7.51(m, 1H), 7.57-7.65(m, 1H), 9.45(sb, 1H), 10.13(sb, 1H) |

-continued
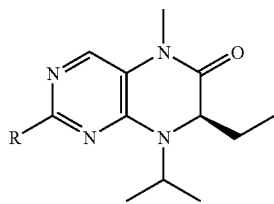
| # | R: | UV max [nm]: | MS(ESI) (M + H)+: | NMR: |
|---|---|---|---|---|
| 16 | (aryl-piperazine-ethyl-N(Me)-ethyl-NMe2 group) | 286 | 568 | 0.71-0.79(m, 3H), 1.26-1.36 (m, 6H), 1.77-1.97(m, 2H), 2.82(s, 6H), 3.19(s, 3H), 3.83(s, 3H), 4.21-4.31(m, 1H), 4.44-4.50(m, 1H), 6.60-6.66(m, 1H), 6.74-6.79(m, 1H), 7.42-7.51(m, 1H), 7.57-7.67(m, 1H), 9.52(s, 1H) |
| 17 | (aryl-piperazine-ethyl-2,6-dimethylpiperidine group) | 286 | 579 | 0.71-0.81(m, 3H), 1.23-2.00 (m, 20H), 4.22-4.35(m, 1H), 4.42-4.50(m, 1H), 6.58-6.66 (m, 1H), 6.72-6.79(m, 1H), 7.40-7.62(m, 2H), 9.40(sb, 1H) |

-continued
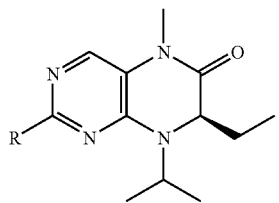
| # | R: | UV max [nm]: | MS(ESI) (M + H)+: | NMR: |
|---|---|---|---|---|
| 18 | HN-X₁ with 2-methoxy-4-(4-(2-piperidin-1-yl-ethyl)piperazin-1-yl)phenyl | 286 | 551 | 0.72-0.78(m, 3H), 1.25-1.35 (m, 6H), 1.38-1.49(m, 1H), 1.67-1.97(m, 7H), 3.53-4.05 (m, 13H), 4.23-4.32(m, 1H), 4.44-4.49(m, 1H), 6.60-6.65 (m, 1H), 6.74-6.79(m, 1H), 7.43-7.63(m, 2H) |
| 19 | HN-X₁ with 2-methoxy-4-(4-(2-pyrrolidin-1-yl-ethyl)piperazin-1-yl)phenyl | 286 | 537 | 0.71-0.78(m, 3H), 1.25-1.35 (m, 6H), 1.76-2.11(m, 6H), 2.98-3.25(m, 9H), 3.54-4.05 (m, 13H), 4.21-4.32(m, 1H), 4.45-4.49(m, 1H), 6.61-6.66 (m, 1H), 6.75-6.79(m, 1H), 7.43-7.51(m, 1H), 7.60(s, 1H), 9.48(s, 1H) |

-continued
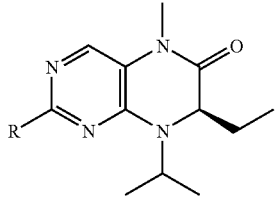
| # | R: | UV max [nm]: | MS(ESI) (M + H)⁺: | NMR: |
|---|---|---|---|---|
| 20 | 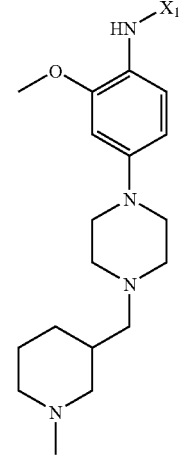 | 282 | 551 | 0.72-0.79(m, 3H), 1.25-1.36 (m, 6H), 1.74-1.97(m, 6H), 2.69-2.75(m, 3H), 3.05-3.22 (m, 7H), 3.51-3.78(m, 4H), 3.80-3.95(m, 5H), 4.21-4.32 (m, 1H), 4.44-4.50(m, 1H), 6.59-6.65(m, 1H), 6.73-6.78 (m, 1H), 7.40-7.50(m, 1H), 7.59(s, 1H), 9.49(m, 1H), 10.63 (sb, 1H), 11.16(sb, 1H) |
| 21 | 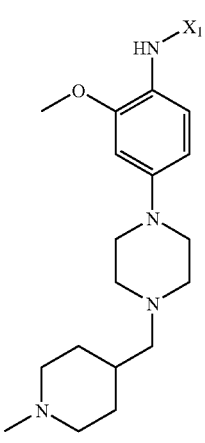 | 282 | 551 | 0.72-0.78(m, 3H), 1.25-1.35 (m, 6H), 1.54-1.65(m, 2H), 1.77-1.97(m, 3H), 2.08-2-21 (m, 3H), 2.67-2.76(m, 4H), 2.87-2.97(m, 2H), 3.05-3.23 (m, 7H), 3.56-3.65 (m, 2H), 3.79-3.90(m, 5H), 4.20-4.30 (m, 1H), 4.45-4.49(m, 1H), 6.59-6.64(m, 1H), 6.72-6.77 (m, 1H), 7.42-7.50(m, 1H), 7.63(s, 1H), 9.54(s, 1H), 10.65 (sb, 1H), 10.16(sb, 1H) |
| 22 | | 282 | 537 | 0.72-0.79(m, 3H), 1.25-1.35 (m, 6H), 1.75-1-99 (M, 2H), 2.08-2.21(m, 2H), 2.71-2.79 (m, 3H), 2.93-3.06(m, 2H), 3.53-3.65(m, 4H), 3.83(m, 3H), 3.86-3.96(m, 2H), 4.20-4.31(m, 1H), 4.44-4.50(m, 1H), 6.59-6.66(m, 1H), 6.73-6.77(m, 1H), 7.41-7.49(m, 1H), 7.54-7.62(m, 1H), 9.47 (sb, 1H), 10.56(sb, 1H), 11.51 (sb, 1H) |

-continued

| # | R: | UV max [nm]: | MS(ESI) (M + H)⁺: | NMR: |
|---|---|---|---|---|
| 23 | (4-(4-cyclohexylpiperazin-1-yl)-2-methoxyphenyl)amino-X₁ | 286 | 522 | 0.72-0.78(m, 3H), 1.17-1.35 (m, 11H), 1.55-1.69(m, 2H), 1.70-1.84(m, 5H), 2.22-2.29 (m, 1H), 2.59-2.66(m, 4H), 3.02-3.09(m, 4H), 3.21(s, 3H), 3.83(s, 3H), 4.20-4.24(m, 1H), 4.44-4.54(m, 1H), 6.42-6.47 (m, 1H), 6.58-6.62(m, 1H), 7.24(s, 1H), 7.72(s, 1H), 7.94-8.00(m, 1H) |
| 24 | (4-(4-isopropylpiperazin-1-yl)-2-methoxyphenyl)amino-X₁ | 286 | 482 | 0.71-0.79(m, 3H), 1.24-1.38 (m, 12H), 1.75-1.98(m, 2H), 3.06-3.34(m, 7H), 3.43-3.55 (m, 3H), 3.82(s, 3H), 3.84-3.92 (m, 2H), 4.44-4.49(m, 1H), 6.58-6.64(m, 1H), 6.72-6.76 (m, 1H), 7.41-7.49(m, 1H), 7.54-7.68(m, 1H), 9.49(m, 1H), 11.20(sb, 1H) |
| 25 | (2-methoxy-4-(4-(tetrahydro-2H-pyran-4-yl)piperazin-1-yl)phenyl)amino-X₁ | 286 | 524 | 0.72-0.79(m, 3H), 1.26-1.36 (m, 6H), 1.77-1.97(m, 4H), 2.17-2.25(m, 2H), 2.70-2.80 (m, 2H), 3.04-3.14(m, 2H), 3.19(s, 3H), 3.81(s, 3H), 3.85-4.02(m, 6H), 4.22-4.31(m, 1H), 4.44-4.49(m, 1H), 6.60-6.66(m, 1H), 6.73-6.78(m, 1H), 7.37-7.45(m, 1H), 7.52-7.62(m, 1H), 9.46(sb, 1H), 11.29(sb, 1H) |

-continued

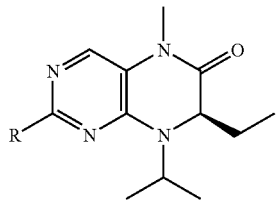

| # | R: | UV max [nm]: | MS(ESI) (M + H)+: | NMR: |
|---|---|---|---|---|
| 26 | (HN-X₁ attached to 3-methoxy-4-aminophenyl-piperidin-1-yl-azetidine) | 286 | 494 | 0.70-0.79(m, 3H), 1.25-1.36 (m, 6H), 1.53-1.64(m, 1H), 1.72-2.02(m, 4H), 2.10-2.25 (m, 3H), 2.72-2.88(m, 2H), 3.03-3.10(m, 1H), 3.19(s, 3H), 3.76-3.90(m, 6H), 3.95-4.14 (m, 2H), 4.22-4.32(m, 1H), 4.44-4.49(m, 1H), 6.57-6.85 (m, 2H), 7.36-7.66(m, 2H), 9.31(sb, 1H), 9.43-9.55(m, 1H) |
| 27 | (HN-X₁ attached to 3-methoxyphenyl-NH-(1-benzylpiperidin-4-yl)) | 262, 286 | 544 | 0.70-0.79(m, 3H), 1.21-1.45 (m, 8H), 1.56-1.68(m, 1H), 1.69-1.82(m, 1H), 1.84-1.96 (m, 2H), 2.01-2.20(m, 2H), 2.71-2.88(m, 2H), 3.20(s, 3H), 3.43-3.56(m, 2H), 3.74(s, 3H), 4.16-4.22(m, 1H), 4.37-4.47 (m, 1H), 5.05-5.17(m, 1H), 6.08-6.15(m, 1H), 6.25-6.32 (m, 1H), 7.13(s, 1H), 7.19-7.37 (m, 5H), 7.60-7.69(m, 2H) |
| 28 | (HN-X₁ attached to 3-methoxyphenyl-NH-(1-ethoxycarbonylpiperidin-4-yl)) | 266, 290 | 526 | (measured in DMSO with HCl) 0.73-0.81(m, 3H), 1.16-1.23 (m, 3H), 1.26-1.33(m, 6H), 1.44-1.58(m, 2H), 1.77-2.02 (m, 4H), 2.78-2.94(m, 2H), 3.23(s, 3H), 3.67-3.78(m, 1H), 3.88(s, 3H), 4.00-4.13(m, 4H), 4.20-4.30(m, 1H), 4.46-4.53 (m, 1H), 6.95-7.02(m, 1H), 7.10-7.15(m, 1H), 7.65-7.75 (m, 2H), 9.66(s, 1H) |

-continued
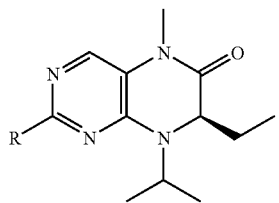
| # | R: | UV max [nm]: | MS(ESI) (M + H)+: | NMR: |
|---|---|---|---|---|
| 29 | HN-X₁, 2-methoxyphenyl with NH-CH₂-triazole-CH₂-morpholine | 226, 286 | 551 | 0.70-0.79(m, 3H), 1.20-1.35 (m, 6H), 1.74-1.98(m, 2H), 3.72(s, 3H), 3.78-4.03(m, 5H), 4.19 (sb, 1H), 4.40-4.51(m, 3H), 4.58(s, 2H), 6.27-6.33(m, 2H), 6.44-6.50(m, 1H), 7.09-7.17(m, 1H), 7.46(sb, 1H), 9.36 (sb, 1H) |
| 30 | HN-X₁, 2-methoxyphenyl with NH-cyclohexyl-morpholine | 226, 266, 290 | 538 | 0.70-0.80(m, 3H), 1.22-1.40 (m, 8H), 1.56-1.69(m, 2H), 1.75-1.97(m, 2H), 2.05-2.25 (m, 4H), 3.76(s, 3H), 3.84-4.01 (m, 4H), 4.23(sb, 1H), 4.43-4.49(m, 1H), 6.37-6.69(m, 2H), 7.31(sb, 1H), 7.57(sb, 1H), 9.44(sb, 1H), 11.10(sb, 1H) |
| 31 | HN-X₁, 2-methoxyphenyl with 4-methylpiperazine | 226, 282 | 454 | 0.71-0.80(m, 3H), 1.26-1.37 (m, 6H), 1.75-1.99(m, 2H), 2.79-2.86(m, 3H), 3.82(s, 3H), 3.84-3.92(m, 2H), 4.20-4.31 (m, 1H), 4.44-4.50(m, 1H), 6.57-6.64(m, 1H), 6.72-6.76 (m, 1H), 7.40-7.47(m, 1H), 7.53-7.62(m, 1H), 9.42-9.50 (m, 1H), 10.72-10.87(m, 1H) |

-continued

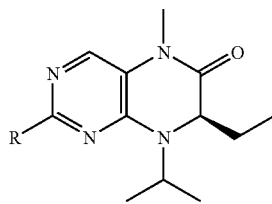

| # | R: | UV max [nm]: | MS(ESI) (M + H)+: | NMR: |
|---|---|---|---|---|
| 32 | HN-X₁, 2-methoxy-4-(propylamino)phenyl | 226, 266, 290 | 413 | (measured in DMSO with HCl) 0.76-0.84(m, 3H), 0.96-1.04 (m, 3H), 1.30-1.39(m, 6H), 1.67-1.78(m, 2H), 1.81-1.91 (m, 1H), 1.97-2.07(m, 1H), 3.26(s, 3H), 3.31-3.37(m, 2H), 3.94(s, 3H), 4.31-4.40(m, 1H), 4.49-4.54(m, 1H), 7.16-7.21 (m, 1H), 7.30-7.35(m, 1H), 7.77(s, 1H), 7.90-7.96(m, 1H), 9.63(s, 1H) |
| 33 | HN-X₁, 2-methoxy-4-((1-methylpiperidin-4-yl)amino)phenyl | 226, 262, 286 | 468 | 0.72-0.78(m, 3H), 1.22-1.38 (m, 6H), 1.73-1.97(m, 4H), 2.05-2.14(m, 2H), 2.68-2.76 (m, 3H), 3.19(s, 3H), 3.49-3.56 (m, 1H), 4.22(sb, 1H), 4.44-4.47(m, 1H), 6.30-6.57(m, 2H), 7.23(sb, 1H), 7.53(sb, 1H), 9.46(sb, 1H), 10.75(sb, 1H) |
| 34 | HN-X₁, 2-methoxy-4-((2-(dimethylamino)ethyl)amino)phenyl | 226, 262, 282 | 442 | 0.72-0.79(m, 3H), 1.22-1.38 (m, 6H), 1.76-1.86(m, 1H), 1.87-1.97(m, 1H), 2.80(s, 6H), 3.19-3.24(m, 2H), 3.46-3.52 (m, 2H), 4.22(sb, 1H), 4.43-4.48(m, 1H), 6.27-6.32(m, 1H), 6.39-6.44(m, 1H), 7.19 (sb, 1H), 7.51(sb, 1H), 9.42(sb, 1H), 10.77(sb, 1H |
| 35 | HN-X₁, 2-methoxy-4-(isopropylamino)phenyl | 266, 295 | 413 | 0.71-0.79(m, 3H), 1.08-1.15 (m, 6H), 1.24-1.32(m, 6H), 1.56-1.83(m, 2H), 3.20(s, 3H), 3.47-3.57(m, 1H), 3.74(s, 3H), 4.16-4.21(m, 1H), 4.35-4.46 (m, 1H), 4.95-5.07(m, 1H), 6.06-6.13(m, 1H), 6.24-6.30 (m, 1H), 7.13(s, 1H), 7.62-7.70 (m, 2H) |

EXAMPLE 36

(R)-2-{4-[4-(3-amino-propyl)-piperazin-1-yl]-2-methoxy-phenylamino}-7-ethyl-8-isopropyl-5-methyl-7,8-dihydro-5H-pteridin-6-one

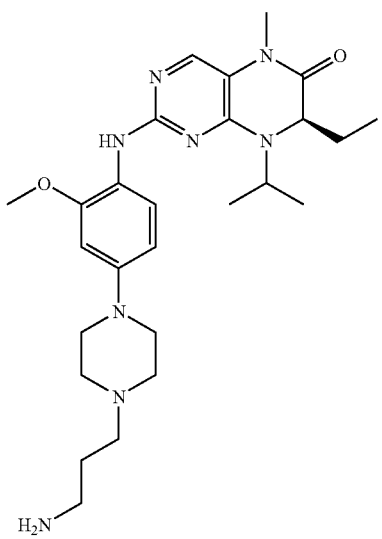

50 mg (0.186 mmol) (R)-2-chloro-7-ethyl-8-isopropyl-5-methyl-7,8-dihydro-5H-pteridin-6-one are dissolved in 0.5 ml of ethanol and 1 ml distilled water, combined with 25 µl of a 33% aqueous hydrochloric acid and 82 mg (0.206 mmol) benzyl 2{3-[4-(4-amino-3-methoxy-phenyl)-piperazin-1-yl]-propyl}-carbamate (method 1) and stirred for 3 h at 100° C.

Then the solvent is eliminated in vacuo. The crude product is purified by column chromatography. The carrier material used is C18-RP gel and a gradient is run through which consists of 95% water and 5% acetonitrile at the starting point and 5% water and 95% acetonitrile at the finishing point.

33 mg (0.045 mmol) benzyl (3-{4-[4-((R)-7-ethyl-8-isopropyl-5-methyl-6-oxo-5,6,7,8-tetrahydro-pteridin-2-ylamino)-3-methoxy-phenyl]-piperazin-1-yl}-propyl)-carbamate are taken up in 5 ml of methanol combined with 4 mg palladium hydroxide and stirred for 24 h at 20° C. and 7 bar hydrogen pressure. Then the catalyst is filtered off and the solvent is eliminated in vacuo.

Yield: 26 mg (0.040 mmol; 22%)
UV max: 282 nm
MS (ESI): 497 (M+H)+

$^1$H-NMR: 0.71-0.78 (m, 3H), 1.25-1.35 (m, 6H), 1.69-1.92 (m, 2H), 2.02-215 (m, 2H), 2.89-2.98 (m, 2H), 3.75-3.91 (m, 5H), 4.30-4.43 (m, 2H), 6.56-6.62 (m, 1H), 6.70-6.75 (m, 1H), 7.60-7.70 (m, 1H), 8.02-8.15 (m, 1H).

EXAMPLE 37

(R)-2-{4-[4-(3-amino-butyl)-piperazin-1-yl]-2-methoxy-phenylamino}-7-ethyl-8-isopropyl-5-methyl-7,8-dihydro-5H-pteridin-6-one

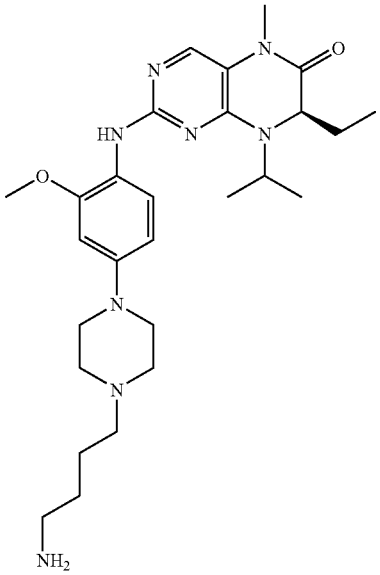

This substance is prepared analogously to Example 38.
UV max: 282 nm
MS (ESI): 511 (M+H)+

$^1$H-NMR: 0.72-0.78 (m, 3H), 1.28-1.35 (m, 6H), 1.59-1.67 (m, 2H), 1.69-1.91 (m, 4H), 2.79-2.87 (m, 2H), 3.78-3.89 (m, 5H), 4.30-4.45 (m, 2H), 6.55-6.60 (m, 1H), 6.70-6.74 (m, 1H), 7.60-7.70 (m, 1H), 7.94 (s, 1H)

As has been found, the compounds of general formula (I) are characterised by their many possible applications in the therapeutic field. Particular mention should be made of those applications for which the inhibition of specific cell cycle kinases, particularly their inhibiting effect on the proliferation of cultivated human tumour cells, and also on the proliferation of other cells, such as e.g. endothelial cells, plays a part.

As demonstrated by DNA staining followed by FACS analysis, the inhibition of proliferation brought about by the compounds according to the invention is mediated by the arrest of the cells above all in the G2/M phase of the cell cycle. The cells arrest, depending on the cells used, for a specific length of time in this cell cycle phase before programmed cell death is initiated. An arrest in the G2/M phase of the cell cycle is initiated e.g. by the inhibition of specific cell cycle kinases. On the basis of their biological properties the compounds of general formula I according to the invention, their isomers and the physiologically acceptable salts thereof are suitable for treating diseases characterised by excessive or anomalous cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tmours; skin diseases (e.g. psoriasis); bone diseases; cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment (Davis et al., 2001). The new compounds may be used for the prevention, short- or long-term treatment of the above-mentioned diseases, also in combination with other active substances used for the same indications, e.g. cytostatics, hormones or antibodies.

The activity of the compounds according to the invention was determined in the PLK1 inhibition assay, in the cytotoxicity test on cultivated human tumour cells and/or in a FACS analysis, e.g. on HeLa S3 cells. In both test methods the compounds exhibited a good to very good activity, i.e. for example an $EC_{50}$ value in the HeLa S3 cytotoxicity test of less than 5 µmol/L, generally less than 1 µmol/L, and an $IC_{50}$ value in the PLK1 inhibition assay of less than 1 gmol/L.

PLK-1 Kinaseassay

Enzyme Preparation:

Recombinant human PLK1 enzyme linked to GST at its N-terminal end is isolated from insect cells infected with baculovirus (Sf21). Purification is carried out by affinity chromatography on glutathione sepharose columns.

$4 \times 10^7$ Sf21 cells (*Spodoptera frugiperda*) in 200 ml of Sf-900 II Serum free insect cell medium (Life Technologies) are seeded in a spinner flask. After 72 hours' incubation at 27° C. and 70 rpm, $1 \times 10^8$ Sf21 cells are seeded in a total of 180 ml medium in a new spinner flask. After another 24 hours, 20 ml of recombinant Baculovirus stock suspension are added and the cells are cultivated for 72 hours at 27° C. at 70 rpm. 3 hours before harvesting, okadaic acid is added (Calbiochem, final concentration 0.1 µM) and the suspension is incubated further. The cell number is determined, the cells are removed by centrifuging (5 minutes, 4° C., 800 rpm) and washed 1× with PBS (8 g NaCl/l, 0.2 g KCU/l, 1.44 g $Na_2HPO_4$/l, 0.24 g $KH_2PO4$/l). After centrifuging again the pellet is flash-frozen in liquid nitrogen. Then the pellet is quickly thawed and resuspended in ice-cold lysing buffer (50 mM HEPES pH 7.5, 10 mM $MgCl_2$, 1 mM DTT, 5 µg/ml leupeptin, 5 µg/ml aprotinin, 100 µM NaF, 100 µM PMSF, 10 mM B-glycerolphosphate, 0.1 mM $Na_3VO_4$, 30 mM 4-nitrophenylphosphate) to give $1 \times 10^8$ cells/17.5 ml. The cells are lysed for 30 minutes on ice. After removal of the cell debris by centrifugation (4000 rpm, 5 minutes) the clear supernatant is combined with glutathione sepharose beads (1 ml resuspended and washed beads per 50 ml of supernatant) and the mixture is incubated for 30 minutes at 4° C. on a rotating board. Then the beads are washed with lysing buffer and the recombinant protein is eluted from the beads with 1 ml eluting buffer/ml resuspended beads (eluting buffer: 100 mM Tris/HCl pH=8.0, 120 mM NaCl, 20 mM reduced glutathione (Sigma G-4251), 10 mM $MgCl_2$, 1 mM DTT). The protein concentration is determined by Bradford Assay.

Assay Procedure

The following components are combined in a well of a 96-well round-bottomed dish (Greiner bio-one, PS Microtitre plate No. 650101):

10 µl of the compound to be tested in variable concentrations (e.g. beginning at 300 µM, and dilution to 1:3) in 6% DMSO, 0.5 mg/ml casein (Sigma C-5890), 60 mM β-glycerophosphate, 25 mM MOPS pH=7.0, 5 mM EGTA, 15 mM $MgCl_2$, 1 mM DTT 20 µl substrate solution (25 mM MOPS pH=7.0, 15 mM $MgCl_2$, 1 mM DTT, 2.5 mM EGTA, 30 mM β-glycerophosphate, 0.25 mg/ml casein)

20 µl enzyme dilution (1:100 dilution of the enzyme stock in 25 mM MOPS pH=7.0, 15 mM $MgCl_2$, 1 mM DTT)

10 µl ATP solution (45 µM ATP with $1.11 \times 10^6$ Bq/ml gamma-P33-ATP).

The reaction is started by adding the ATP solution and continued for 45 minutes at 30° C. with gentle shaking (650 rpm on an IKA Schuttler MTS2). The reaction is stopped by the addition of 125 µl of ice-cold 5% TCA per well and incubated on ice for at least 30 minutes. The precipitate is transferred by harvesting onto filter plates (96-well microtitre filter plate: UniFilter-96, GF/B; Packard; No.6005177), then washed four times with 1% TCA and dried at 60° C. After the addition of 3511 scintillation solution (Ready-Safe; Beckmann) per well the plate is sealed shut with sealing tape and the amount of P33 precipitated is measured with the Wallac Betacounter. The measured data are evaluated using the standard Graphpad software (Levenburg-Marquard Algorhythmus).

Measurement of Cytotoxicity on Cultivated Human Tumour Cells

To measure cytotoxicity on cultivated human tumour cells, cells of cervical carcinoma tumour cell line HeLa S3 (obtained from American Type Culture Collection (ATCC)) were cultivated in Ham's F12 Medium (Life Technologies) and 10% foetal calf serum (Life Technologies) and harvested in the log growth phase. Then the HeLa S3 cells were placed in 96-well plates (Costar) at a density of 1000 cells per well and incubated overnight in an incubator (at 37° C. and 5% $CO_2$), while on each plate 6 wells were filled with medium alone (3 wells as the medium control, 3 wells for incubation with reduced AlamarBlue reagent). The active substances were added to the cells in various concentrations (dissolved in DMSO; DMSO final concentration: 0.1%) (in each case as a triple measurement). After 72 hours incubation 20 µl AlamarBlue reagent (AccuMed International) were added to each well, and the cells were incubated for a further 5-7 hours. As a control, 20 µl reduced AlamarBlue reagent was added to each of 3 wells (AlamarBlue reagent, which was autoclaved for 30 min). After incubation the colour change of the AlamarBlue reagent in the individual wells was determined in a Perkin Elmer fluorescence spectrophotometer (excitation 530 nm, emission 590 nm, slits 15, integrate time 0.1). The amount of AlamarBlue reagent reacted represents the metabolic activity of the cells. The relative cell activity was calculated as a percentage of the control (HeLa S3 cells without inhibitor) and the active substance concentration which inhibits the cell activity by 50% (IC50) is derived. The values were calculated from the average of three individual measurements—with correction of the dummy value (medium control).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, 0.4 million HeLa S3 cells were seeded onto a 75 cm2 cell culture flask, and after 24 h either 0.1% DMSO was added as control or the substance was added in various concentrations (in 0.1% DMSO). The cells were incubated for 24 h with the substance or with DMSO before the cells were washed 2× with PBS and then detached with trypsin/EDTA. The cells were centrifuged (1000 rpm, 5 min, 4° C.), and the cell pellet was washed 2× with PBS before the cells were resuspended in 0.1 ml PBS. Then the cells were fixed with 80% ethanol for 16 hours at 4° C. or alternatively for 2 hours at −20° C. The fixed cells ($10^6$ cells) were centrifuged (1000 rpm, 5 min, 4° C.), washed with PBS and then centrifuged again. The cell pellet was resuspended in 2 ml Triton X-100 in 0.25% PBS, and incubated on ice for 5 min before 5 ml PBS were added and the mixture was centrifuged again. The cell pellet was resuspended in 350 µl PI staining solution (0.1 mg/ml RNase A, 10 µg/ml prodium iodide in 1×PBS). The cells were incubated for 20 min in the dark with the staining buffer before being transferred into sample measuring containers for the FACS scan. The DNA measurement was carried out in a Becton Dickinson FACS Analyzer, with an argon laser (500 mW, emission 488 nm), and the DNA Cell Quest Programme (BD). The logarithmic PI fluorescence was determined with a band-pass filter (BP 585/42). The cell populations in the individual cell cycle phases were quantified using the ModFit LT Programme made by Becton Dickinson.

The compounds according to the invention were also tested accordingly for other tumour cells. For example, these compounds are effective on carcinomas of all kinds of tissue (e.g. breast (MCF7); colon (HCT116), head and neck (FaDu), lung (NCI-H460), pancreas (BxPC-3), prostate (DU145)), sarcomas (e.g. SK-UT-1B), leukaemias and lymphomas (e.g. HL-60; Jurkat, THP-1) and other tumours (e.g. melanomas (BRO), gliomas (U-87MG)) and could be used for such indications. This is evidence of the broad applicability of the compounds according to the invention for the treatment of all kinds of tumour types.

The compounds of general formula (I) may be used on their own or in conjunction with other active substances according to the invention, optionally also in conjunction with other pharmacologically active substances.

Suitable preparations include for example tablets, capsules, suppositories, solutions, particularly solutions for injection (s.c., i.v., i.m.) and infusion, elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A Compound of the formula (1)

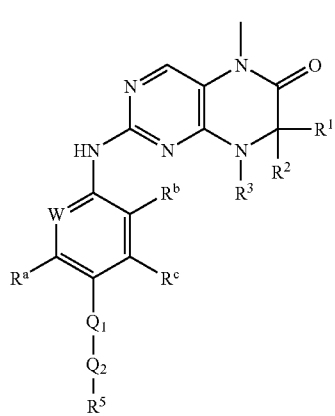

(1)

wherein

W denotes N or C—$R^4$, $R^1$, $R^2$ each independently of one another denote hydrogen or optionally mono- or polysubstituted $C_{1-6}$alkyl, $C_{2-6}$alkenyl, $C_{2-6}$alkynyl;

or $R^1$ and $R^2$ together form a saturated or partially unsaturated 2-5-membered alkyl bridge, wherein a —$CH_2$- group may be replaced by O, S, —$NR^8$ or a —CH- group may be replaced by N;

$R^3$ denotes hydrogen or a group selected from among optionally mono- or polysubstituted $C_{1-12}$alkyl, $C_{2-12}$alkenyl, $C_{2-12}$-alkynyl, cycloalkyl, aryl, heteroaryl and heterocyclyl, wherein the substituent(s) may be identical or different and are selected from among halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen, or $R^1$ and $R^3$ or $R^2$ and $R^3$ together form a saturated or partially unsaturated 2-5-membered alkyl bridge, wherein a —$CH_2$- group may be replaced by O, S, —$NR^8$ or a —CH- group may be replaced by N;

$R^4$ denotes a group selected from among hydrogen, —CN, hydroxy, halogen, —$OR^8$ and —$NR^6R^7$, or a group selected from among optionally mono- or polysubstituted $C_{1-6}$alkyl, $C_{2-6}$alkenyl, $C_{2-6}$alkynyl, $C_{1-5}$alkyloxy, $C_{2-5}$alkenyloxy, $C_{2-5}$alkynyloxy, $C_{1-6}$alkylthio, $C_{1-6}$alkylsulphoxo and $C_{1-6}$alkylsulphonyl, while the substituent(s) may be identical or different and are selected from among halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$Q_1$ denotes a group selected from among optionally mono- or polysubstituted piperidinyl, piperazinyl, homopiperazinyl, pyrrolidinyl, tropenyl, azacycloheptyl and —$N(R^8)$—$(CH_2)_n$—;

while the substituent(s) may be identical or different and are selected from among halogen, —$NO_2$, $R^8$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$Q_2$ is either absent or denotes a group selected from among optionally mono- or polysubstituted $C_{1-16}$alkylene, $C_{2-16}$alkenylene, $C_{2-16}$alkynylene, cycloalkyl, aryl, heterocyclyl and heteroaryl while the substituent(s) may be identical or different and are selected from among halogen, —$NO_2$, $R^8$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^5$ denotes hydrogen or a group selected from among optionally mono- or polysubstituted $C_{1-6}$alkyl, $C_{2-16}$alkenyl, $C_{2-16}$alkynyl, cycloalkyl, aryl, heterocyclyl and heteroaryl, wherein the substituent(s) may be identical or different and are selected from among halogen, —$NO_2$, $R^8$, —$OR^8$, —$C(=O)R^8$, —$C(=O)OR^8$, —$C(=O)NR^8R^9$, —$NR^8R^9$, —$NR^8COR^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^a$, $R^b$ and $R^c$ each independently of one another denote a group selected from among hydrogen, halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

or an optionally mono- or polysubstituted group selected from among $C_{1-6}$alkyl, $C_{2-6}$alkenyl, $C_{2-6}$alkynyl, $C_{3-6}$cycloalkyl, aryl, heterocyclyl and heteroaryl, while the substituents may be identical or different and are selected from among halogen, —$NO_2$, —$OR^8$, —$C(=O)R^8$, —$C(=O)OR^8$, —$C(=O)NR^8R^9$, —$NR^8R^9$, —$NR^8COR^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^6$, $R^7$ each independently of one another denote hydrogen or a group selected from among optionally mono- or polysubstituted $C_{1-16}$alkyl, $C_{2-16}$alkenyl, $C_{2-16}$alkynyl, cycloalkyl, aryl, heterocyclyl and heteroaryl while the substituent(s) may be identical or different and are selected from among halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen;

$R^8$, $R^9$, $R^{10}$ each independently of one another denote hydrogen or a group selected from among optionally substituted $C_{1-8}$alkyl, $C_{2-8}$alkenyl, $C_{2-8}$alkynyl, cycloalkyl, aryl, heterocyclyl and heteroaryl, wherein the substituent(s) may be identical or different and are selected from among halogen, methyl, ethyl, amino, methylamino, dimethylamino, —OH and pseudohalogen;

n denotes 0, 1, 2 or 3 optionally in the form of the tautomers, racemates, enantiomers, diastereomers and mixtures thereof, and optionally the pharmacologically acceptable acid addition salts thereof.

2. The Compound according to claim 1, wherein W denotes C—$R^4$.

3. The Compound according to claim 2, wherein $R^b$ denotes a group selected from among hydrogen, —F, —Cl, methyl and ethyl.

4. The Compound according to claim 3, wherein $R^a$, $R^c$ each independently of one another denote hydrogen or fluorine;

or an optionally mono- or polysubstituted group selected from among $C_{1-2}$alkyl, $C_2$alkenyl, $C_2$alkynyl, $C_{3-6}$cycloalkyl, aryl, heterocyclyl and heteroaryl, while the substituents may be identical or different and are selected from among hydrogen, halogen, —$NO_2$, —$OR^8$, —$C(=O)R^8$, —$C(=O)OR^8$, —$C(=O)NR^8R^9$, —$NR^8R^9$, —$NR^8C(=O)R^9$, —$NR^8C(=O)OR^9$, —$NR^8C(=O)NR^9R^{10}$, —$NR^8C(=O)ONR^9R^{10}$, —$NR^8SO_2R^9$, —$N=CR^8R^9$, —$SR^8$, —$SOR^8$, —$SO_2R^8$, —$SO_2NR^8R^9$, —$NR^8SO_2NR^9R^{10}$, —$OSO_2NR^8R^9$ and pseudohalogen.

5. The Compound according to claim 4, wherein $R^a$, $R^c$ each independently of one another denote hydrogen or fluorine.

6. The Compound according to claim 5, wherein $R^1$, $R^2$ each independently of one another denote hydrogen or optionally substituted $C_{1-3}$alkyl, $C_{2-3}$alkenyl or $C_{2-3}$-alkynyl, or $R^1$ and $R^2$ together form a saturated or partially unsaturated 2-5-membered alkyl bridge wherein a —$CH_2$- group may be replaced by O, S, —$NR^8$ or a —CH- group may be replaced by N.

7. The Compound according to claim 6, wherein $R^5$ denotes hydrogen, methyl, ethyl, hydroxy, methoxy, ethoxy, amino, methylamino, dimethylamino, F, Cl, Br, O-propargyl, CN, methylthio, $CONH_2$, ethynyl, propynyl, butynyl or allyl.

8. The Compound according to claim 7, wherein $Q_1$ denotes piperazinyl or homopiperazinyl.

9. A method of treating a disease chosen from breast (MCF7, MaTu-MDR), colon (HCT116), head and neck (FaDu), lung (NCI-H460), pancreatic (BxPC-3), and prostate cancer (DU145), cervical carcinoma (HeLa S3), sarcomas (SK-UT-1B), leukemias and lymphomas (HL-60, Jurkat, THP-1), melanoma (BRO) and glioma (U-87MG), comprising administering to a patient a therapeutically effective amount of a compound of formula I according to claim 1.

10. A Pharmaceutical composition comprising a pharmaceutically effective amount of a compound of the formula (I) according to claim 1 optionally with pharmaceutically acceptable excipients and/or carriers.

* * * * *